(12) United States Patent
Yu et al.

(10) Patent No.: US 6,500,620 B2
(45) Date of Patent: Dec. 31, 2002

(54) METHODS FOR AMPLIFYING AND DETECTING MULTIPLE POLYNUCLEOTIDES ON A SOLID PHASE SUPPORT

(75) Inventors: Zailin Yu, San Leandro, CA (US); Zaoyuan Peng, Palo Alto, CA (US); Qianjin Hu, Castro Valley, CA (US)

(73) Assignee: Mergen Ltd., San Leandro, CA (US)

( * ) Notice: Subject to any disclaimer, the term of this patent is extended or adjusted under 35 U.S.C. 154(b) by 0 days.

(21) Appl. No.: 09/741,983

(22) Filed: Dec. 19, 2000

(65) Prior Publication Data

US 2001/0036632 A1 Nov. 1, 2001

Related U.S. Application Data

(60) Provisional application No. 60/173,618, filed on Dec. 29, 1999.

(51) Int. Cl.[7] .................. C12Q 1/68; C12P 19/34; C07H 21/04
(52) U.S. Cl. ................ 435/6; 435/91.1; 435/91.2; 536/24.33
(58) Field of Search .............. 435/6, 91.1, 91.2, 435/810; 536/24.33

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,800,159 A | 1/1989 | Mullis et al. |
| 5,405,746 A | 4/1995 | Uhlen |
| 5,419,966 A | 5/1995 | Reed et al. |
| 5,436,327 A | 7/1995 | Southern et al. |
| 5,470,967 A | 11/1995 | Huie et al. |
| 5,556,752 A | 9/1996 | Lockhart et al. |
| 5,641,658 A | 6/1997 | Adams et al. |
| 5,643,765 A | 7/1997 | Willey |
| 5,700,637 A | 12/1997 | Southern |
| 5,714,331 A | 2/1998 | Buchardt et al. |
| 5,723,320 A | 3/1998 | Dehlinger |
| 5,744,305 A | 4/1998 | Fodor et al. |
| 5,747,251 A | 5/1998 | Carson et al. |
| 5,750,380 A | 5/1998 | Itakura et al. |
| 5,759,779 A | 6/1998 | Dehlinger |
| 5,770,456 A | 6/1998 | Holmes |
| 5,770,722 A | 6/1998 | Lockhart et al. |
| 5,800,992 A | 9/1998 | Fodor et al. |
| 5,807,522 A | 9/1998 | Brown et al. |
| 5,807,680 A | 9/1998 | Sutcliffe et al. |
| 5,817,479 A | 10/1998 | Au-Young et al. |
| 5,831,070 A | 11/1998 | Pease et al. |
| 5,837,832 A | 11/1998 | Chee et al. |
| 5,856,174 A | 1/1999 | Lipshutz et al. |
| 5,858,652 A | 1/1999 | Laffler et al. |
| 5,861,242 A | 1/1999 | Chee et al. |
| 5,891,625 A | 4/1999 | Buchardt et al. |
| 5,919,523 A | 7/1999 | Sundberg et al. |
| 5,922,617 A | 7/1999 | Wang et al. |
| 5,928,905 A | 7/1999 | Stemmer et al. |

(List continued on next page.)

OTHER PUBLICATIONS

Brown, P. O. and Botstein, D. (1999). "Exploring the New World of the Genome with DNA Microarrays," *Nature Genetics Supplement* 21:33–37.

(List continued on next page.)

*Primary Examiner*—Kenneth R. Horlick
(74) *Attorney, Agent, or Firm*—Morrison & Foerster LLP

(57) ABSTRACT

Methods for solid phase polymerase-mediated amplification using immobilized primers on a microarray are provided for detecting and cloning multiple target polynucleotides. The methods, compositions and kits provided herein are useful for research and clinical applications, particularly for large scale assays of genetic information in biological samples of interest.

34 Claims, 6 Drawing Sheets

U.S. PATENT DOCUMENTS

| | | | |
|---|---|---|---|
| 5,948,649 | A | 9/1999 | Stewart et al. |
| 5,958,698 | A | 9/1999 | Chetverin et al. |
| 6,017,738 | A | 1/2000 | Morris et al. |
| 6,054,270 | A | 4/2000 | Southern |
| 6,060,288 | A * | 5/2000 | Adams et al. ............. 435/91.1 |
| 6,150,095 | A | 11/2000 | Southern et al. |
| 6,153,379 | A | 11/2000 | Caskey et al. |
| 6,221,635 | B1 * | 4/2001 | Rovera et al. ............. 435/91.2 |
| 6,300,070 | B1 * | 10/2001 | Boles et al. ................... 435/6 |

OTHER PUBLICATIONS

Chakravarti, A. (1999). "Population Genetics—Making Sense out of Sequence," *Nature Genetics Supp.* 21:56–60.

Cho, R. J. et al. (1998). "Parallel Analysis of Genetic Selections Using Whole Genome Oligonucleotide Arrays," *Proc. Natl. Acad. Sci. USA* 95:3752–3757.

Collins F.S. et al. (Nov. 28, 1997). "Variations on a Theme: Cataloging Human DNA Sequqnce Variation," *Science* 278:1580–1581.

Denis, M. et al. (1997). "Development of a Semiquantitative PCR Assay Using Internal Standard and Colorimetric Detection on Microwell Plate for Pseudorabies Virus," *Molecular and Cellular Probes* 11:439–448.

Eliaou, J. et al. (1992). "Generic HLA–DRB1 Gene Oligotyping by a Nonradioactive Reverse Dot–Blot Methodology," *Human Immunology* 35:215–222.

Embretson, J. et al. (Mar. 25, 1993). "Massive Covert Infection of Helper T Lymphocytes and Macrophages by HIV During the Incubation Period of AIDS," *Nature* 362:359–362.

Gosden, J. and D. Hanratty. (1993). "PCT In Situ: A Rapid Alternative to In Situ Hybridization for Mapping Short, Low Copy Number Sequences Without Isotopes," *BioTechniques.* 15(1):78–80.

Hacia, J. (Jan. 1999) "Resequencing and Mutational Analysis Using Oligonucleotide Microarrays," *Nature Genetics* 21(1 Suppl.):42–47.

Halford, W. P. (1999). "The Essential Prerequisites for Quantitative RT–PCR," *Nature Biotechnology* 17:835.

Heniford, B.W. et al. (1993). "Variation in Cellular EGF Receptor mRNA Expression Demonstrated by In Situ Reverse Transcriptase Polymerase Chain Reaction," *Nucl. Acid Res.* 21(14):3159–3166.

Kohsaka, H. and D.A. Carson. (1994). "Solid–Phase Polymerase Chain Reaction," *J. Clin. Lab Anal.* 8:452–455.

Long, A.A. et al. (1993). "Comparison of Indirect and Direct In–Situ Polymerase Chain Reaction in Cell Preparations and Tissue Sections. Detection of Viral DNA, Gene Rearrangements and Chromosomal Translocations," *Histochemistry.* 99:151–162.

Nielsen, P.E. et al. (1991). "Sequence–Selective Recognition of DNA by Strand Displacement with a Thymine–Substituted Polyamide," *Science.* 254:1497–1500.

Nielsen, P.E. (1999). "Applications of Peptide Nucleic Acids," *Curr. Opin. Biotechnol.* 10:71–75.

Nuovo G.J. et al. (1993). "Importance of Different Variables for Enhancing In Situ Detection of PCR–Amplified DNA," *PCR Methods and Applications.* 2(4):305–312.

Patterson, B.K. et al. (May 14, 1993). "Detection of HIV–1 DNA and Messenger RNA in Individual Cells by PCR–Driven In Situ Hybridization and Flow Cytometry," *Science.* 260:976–979.

Sambrook, J. et al. (1989). *Molecular Cloning, A Laboratory Manual.* Cold Spring Harbor Laboratory Press: Cold Spring Harbor, NY. pp. xi–xxxviii (Table of Contents).

Schena, M. and Davis, R.W. (1999). "Genes, Genomes and Chips" in *DNA Microarrays: A Practical Approach.* Ed. M. Schena Oxford University Press: Oxford, UK. pp. 1–16.

Schena, M. et al. (Oct. 20, 1995). "Quantitiative Monitoring of Gene Expression Patterns with a Complementary DNA Microarray," *Science* 270:467–470.

Schena, M. et al. (Oct. 1996). "Parallel Human Genome Analysis: Microarray–Based Expression Monitoring of 1000 Genes," *Proc. Natl. Acad. Sci. USA* 93:10614–10619.

Velculescu, V.E. et al. (1995). "Serial Analysis of Gene Expression," *Science.* 270:484–486.

Zhang, L. et al. (1997). "Gene Expression Profiles in Normal and Cancer Cells," *Science.* 276:1268–1272.

* cited by examiner

OVC1.1 cDNA-cRNA (Hybridization)

OVC1.1 cDNA (PCR)

Fetal Brain cDNA library (Hybridization)

Fetal Brain cDNA library (PCR)

METHODS FOR AMPLIFYING AND DETECTING MULTIPLE POLYNUCLEOTIDES ON A SOLID PHASE SUPPORT

CROSS-REFERENCE TO RELATED APPLICATIONS

This application claims priority of provisional application No. 60/173,618 filed Dec. 29, 1999.

TECHNICAL FIELD OF THE INVENTION

This invention relates generally to the field of nucleic acid biology. More specifically, the invention provides methods and compositions for high-throughput amplification, detection and comparison of gene expressions in biological samples for diagnostic and therapeutic applications.

BACKGROUND

Detection of small quantities of genetic materials represents a major challenge in biological research and clinical diagnosis. Polymerase chain reaction (PCR) provides a powerful tool for in vitro amplification of specific polynucleotide sequences, such as genomic DNA, single stranded cDNA or mRNA, with high sensitivity and specificity. One application of this is the amplification of target gene sequences in biological samples from, for example, environmental, food and medical sources, etc. to allow identification of causative, pathogenic, spoilage or indicator organisms present in the sample.

The basic PCR technique, as described in U.S. Pat. Nos. 4,683,202, 4,683,195, and 4,800,159 (the disclosures of which are incorporated herein by reference), typically involves using two oligonucleotide primers capable of hybridizing to specific nucleic acid sequences flanking a target sequence of interest. By repeating multiple cycles of template denaturation, primer annealing and strand elongation, an exponential duplication of the target sequence can be obtained.

A major technical problem with standard PCR methods is contamination. While PCR provides a sensitive way for detecting and amplifying small amounts of target polynucleotides, it can amplify non-specific nucleic acid sequences, therefore creating false positive products in the final detection and assay. In a standard solution-phase PCR, in which primers bind to templates and initiate nascent strand synthesis in solution, reaction mixtures and products often need to be transferred several times for final detection and assay, increasing the chances for contamination.

Kohsaka and Carson (1994) *J Clin. Lab Anal* 8:452–455 describes a solid-phase PCR approach to allow amplification and detection of a target gene sequence in the same microwell without transfer. One of the two oligonucleotide primers is covalently attached to the wells of a microtiter plate, the other primer remains in solution. The immobilized primer binds to template and initiates the extension of a nascent complementary strand. The newly synthesized strand remains attached to the plate after removal of the template by denaturation and, at the completion of PCR, can be detected with a labeled probe. The solid-phase PCR approach has also been used for a quantitative determination of the target nucleic acid by adding a known amount of an internal competitive DNA template prior to amplification. See, for example, U.S. Pat. No. 5,747,251, the disclosure of which is incorporated herein by reference.

The solid-phase PCR of Kohsaka et al. is limited to detecting one single target polynucleotide in a well on a 96-well microtiter plate. The quantitative solid-phase PCR using competitive template is limited to detecting target from one species or tissue. Furthermore, the amplified products that are attached to plate must be single-stranded in order to be detected by hybridizing with labeled probes, therefore limiting the sensitivity of the detection.

U.S. Pat. No. 5,641,658 (Adams et al.) describes a method for amplifying nucleic acid with two primers bound to a single solid support. The method requires selection of two primers flanking a target sequence and immobilization of both primers onto a solid support. The primer pairs are used to detect and amplify the target polynucleotide on the support. The amplified products are fixed on the support, and two adjacent strands, if reasonably distanced from each other, can further hybridize together to form a "loop." While the two-primer amplification system is promised to be sensitive in detecting the presence or absence of particular target nucleic acid in a sample, the use of two immobilized primers for each target requires a careful arrangement of the primers on the support so that the primer array would allow the formation of the loops and yet would not interfere the amplification of additional strands. In other words, the methods may not be ideal for a high density, high throughput assay.

The pattern of gene expression in a particular biological sample provides significant insights into the molecular fundamentals of almost all biological function and activities. A number of methods are known in the art for detecting and comparing gene expression levels in different biological sources. One standard method for such comparisons is the Northern blot. In this technique, RNA is extracted from the sample and loaded onto any of a variety of gels suitable for RNA analysis, which are then run to separate the RNA by size, according to standard methods (see, e.g., Sambrook, J., et al., Molecular Cloning, A Laboratory Manual. Cold Spring Harbor Laboratory Press, Cold Spring Harbor, N.Y. (2nd ed. 1989)). The gels are then blotted (as described in Sambrook, supra), and hybridized to probes for RNAs of interest.

Sutcliffe, U.S. Pat. No. 5,807,680, teaches a method for the simultaneous identification of differentially expressed mRNAs and measurement of their relative concentrations. The technique, which comprises the formation of cDNA using anchor primers followed by PCR, allows the visualization of nearly every mRNA expressed by a tissue as a distinct band on a gel whose intensity corresponds roughly to the concentration of the mRNA.

Another group of techniques employs analysis of relative transcript expression levels. Four such approaches have recently been developed to permit comprehensive, high throughput analysis. First, cDNA can be reverse transcribed from the RNAs in the samples (as described in the references above), and subjected to single pass sequencing of the 5' and 3' ends to define expressed sequence tags for the genes expressed in the test and control samples. Enumerating the relative representation of the tags from the different samples provides an approximation of the relative representation of the gene transcript within the samples.

Second, a variation on ESTs has been developed, known as serial analysis of gene expression, or "SAGE," which allows the quantitative and simultaneous analysis of a large number of transcripts. The technique employs the isolation of short diagnostic sequence tags and sequencing to reveal patterns of gene expression characteristic of a target function, and has been used to compare expression levels, for example, of thousands of genes in normal and in tumor cells. See, e.g., Velculescu, et al., Science 270:368–369 (1995); Zhang, et al., Science 276:1268–1272 (1997).

Third, approaches have been developed based on differential display. In these approaches, fragments defined by specific sequence delimiters can be used as unique identifiers of genes, when coupled with information about fragment length within the expressed gene. The relative representation of an expressed gene within a cell can then be estimated by the relative representation of the fragment associated with that gene. Examples of some of the several approaches developed to exploit this idea are the restriction enzyme analysis of differentially-expressed sequences ("READS") employed by Gene Logic, Inc., and total gene expression analysis ("TOGA") used by Digital Gene Technologies, Inc. CLONTECH, Inc. (Palo Alto, Calif.), for example, sells the Delta™ Differential Display Kit for identification of differentially expressed genes by PCR.

Fourth, in preferred embodiments, the detection is performed by one of a number of techniques for hybridization analysis. In these approaches, RNA from the sample of interest is usually subjected to reverse transcription to obtain labeled cDNA. The cDNA is then hybridized, typically to oligonucleotides or cDNAs of known sequence arrayed on a chip or other surface in a known order. The location of the oligonucleotide to which the labeled cDNA hybridizes provides sequence information on the cDNA, while the amount of labeled hybridized RNA or cDNA provides an estimate of the relative representation of the RNA or cDNA of interest. Further, the technique permits simultaneous hybridization with two or more different detectable labels. The hybridization results then provide a direct comparison of the relative expression of the samples.

Recent developments in DNA microarray technology make it possible to conduct a large scale assay of a plurality of target molecules on a single solid phase support. U.S. Pat. No. 5,837,832 (Chee et al.) and related patent applications describe immobilizing an array of oligonucleotide probes for hybridization and detection of specific nucleic acid sequences in a sample. Limitations of microarray analysis include the difficulty of detecting nucleic acids that are available for microarray detection only in small volumes and small quantities. As any technology based on nucleic acid hybridization, the sensitivity of the microarray hybridization is limited in large by the number of target nucleic acids available, i.e., the abundance of the gene expression. Presently, these limitations can sometimes be overcome to a certain extent by amplifying a labeling signal (from a fluorescent tag, for example) that is attached to the nucleic acid target. However, it would be of great advantage in the field to develop more effective and sensitive ways to detect multiple target polynucleotides on a microarray.

SUMMARY OF THE INVENTION

The present invention provides a novel approach for amplifying and detecting multiple polynucleotides in a high throughput fashion. In one aspect, the methods involve detecting multiple target polynucleotides in a sample by using a solid phase microarray of primers suitable for solid phase nucleic acid amplification. Each primer is specific to a particular target sequence and groups of different primers are immobilized at discrete positions within the microarray. The immobilized primers enable "in-situ" hybridization and amplification of specific target polynucleotides on a solid-phase support. The nascent strand at each primer site can be detected quantitatively with labels that are incorporated into the strand during amplification. In one preferred embodiment, the amplification means for practicing the invention is PCR. The microarray on a solid phase support can comprise up to about 100,000 groups of primers. As such, the method is useful for detecting up to about 100,000 target polynucleotides in a sample. For most applications, a high number of groups will be desirable, although it is clear that there is no lower limit to the number of groups which can be present on the support.

According to one embodiment of the invention, an immobilized primer is used alone for asymmetric PCR of a particular target polynucleotide that will result in a single complementary strand attached to the solid phase at each primer site and detected optionally with labels incorporated into the strand. According to another embodiment of the invention, another primer for each target polynucleotide is present in solution so that both strands for a target polynucleotide can be synthesized and retained at each primer site for enhanced detection. The solution phase primers can be specific to particular target polynucleotides or, alternatively, can be universal primers capable of binding either all or a sub-population of target polynucleotides.

The present invention also provides methods for detecting and comparing the expression patterns of multiple target polynucleotides from at least two different biological sources, comprising the steps of: a) contacting a sample comprising multiple target polynucleotides from at least two different biological sources with an array of multiple groups of oligonucleotide primers immobilized to a solid phase support, with each group of oligonucleotide primers being selected for a particular target polynucleotide and comprising primers complementary to a sequence of the target polynucleotide, wherein said target polynucleotides from each biological source contain a covalently linked sequence tag that is unique to the biological source; b) performing a first round of polymerase-mediated polynucleotide amplification under conditions suitable for polynucleotide hybridization and amplification, whereby the target polynucleotides from different biological sources serve as initial templates for the synthesis of complementary nascent polynucleotide strands which are extended from the immobilized primers; c) performing a second round of polymerase-mediated polynucleotide amplification in the presence of solution phase primers that hybridize to the sequence tags that are unique to each biological source, wherein the sequence tags serve as primers and the immobilized nascent polynucleotide strands from step b) serve as templates for the synthesis of new amplification products which are extended from the solution phase sequence tags; and d) detecting and comparing the immobilized amplification products of target polynucleotides from different biological sources.

The invention further provides kits for detecting multiple target polynucleotides using either symmetric PCR or asymmetric PCR approach as disclosed herein. The kits comprise a microarray of PCR primers and reagents necessary for PCR reaction and detection. The microarray of primers can comprise up to about 100,000 groups of primers tailored to particular target polynucleotide sequences. In one embodiment of the invention, the kits comprise labeled nucleotides capable of being incorporated into the synthesized strands during PCR reaction.

BRIEF DESCRIPTION OF THE FIGURES

FIG. 6 illustrates the enhancement of hybridization signal by solid phase PCR amplification prior to hybridization.

FIG. 6A illustrates the hybridization signal following standard protocols, whereas

FIG. 6C illustrates the signal following hybridization to a microarray comprising fetal brain cDNA target, whereas

DETAILED DESCRIPTION OF PREFERRED EMBODIMENTS

Figure 1A:
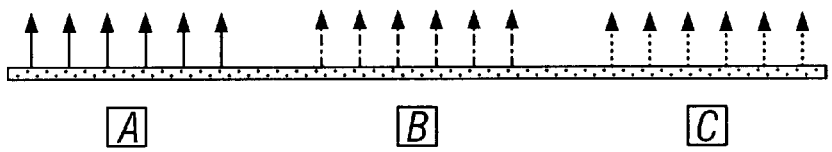
FIGS. 1A–1E depict schematically a solid phase amplification method for amplifying and detecting target polynucleotides (A, B, C), using immobilized primers.
Figure 1B:
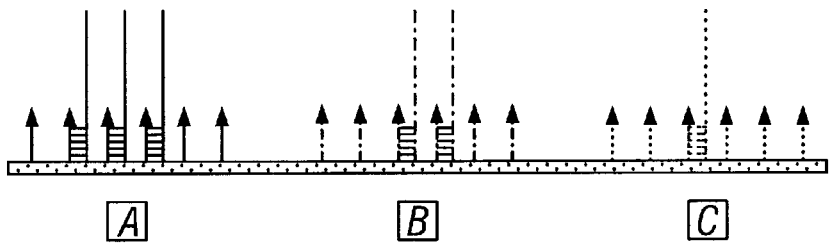
Figure 1C:
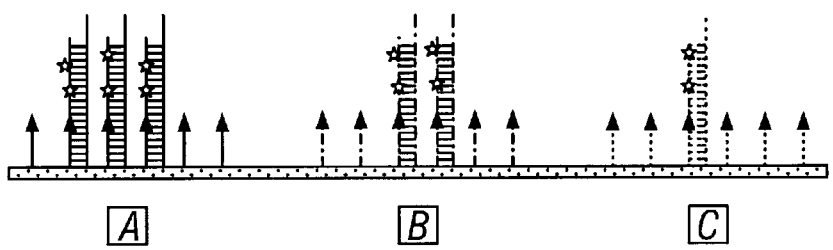
Figure 1D:
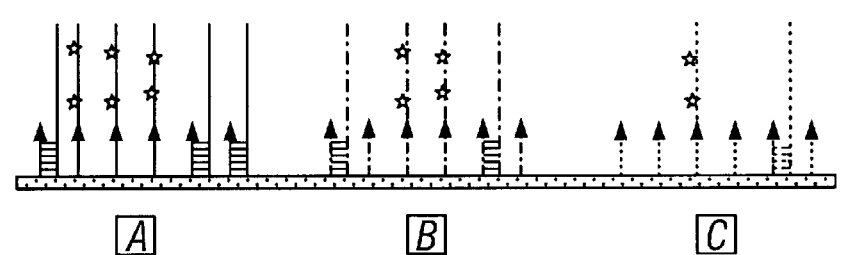
Figure 1E:
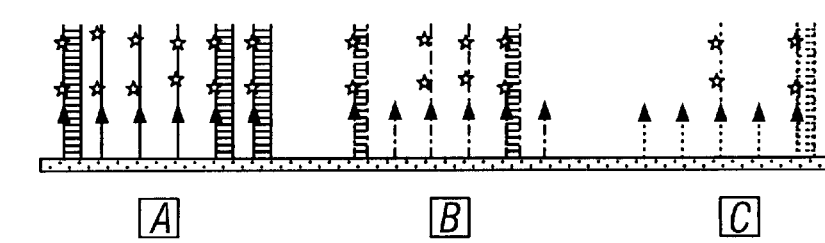
Figure 2A:
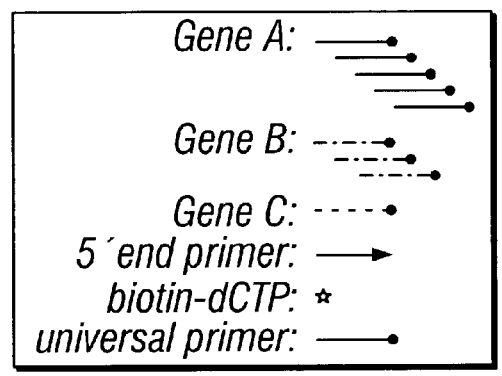
FIGS. 2A–2E depict schematically a solid phase amplification method for amplifying and detecting target polynucleotides (A, B, C), using immobilized primers in combination with solution phase universal primers.
Figure 2A:
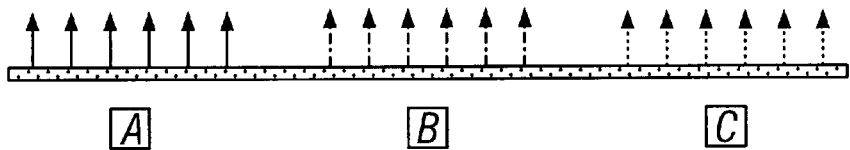
Figure 2B:
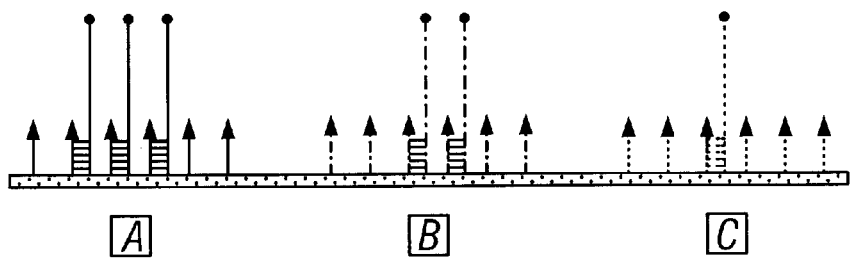
Figure 2C:
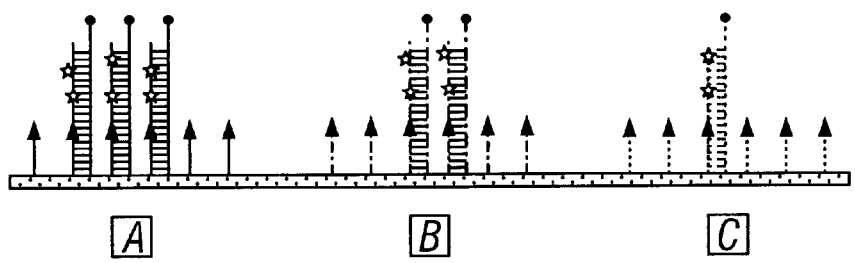
Figure 2D:
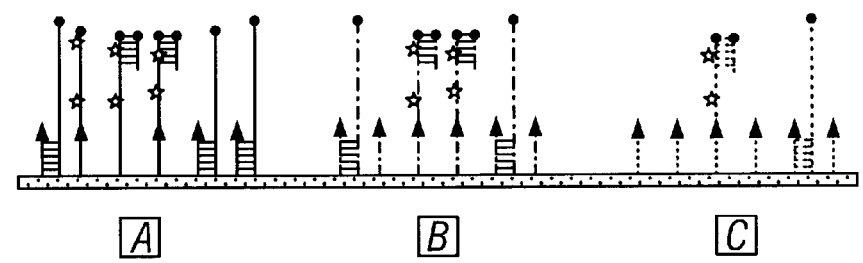
Figure 2E:
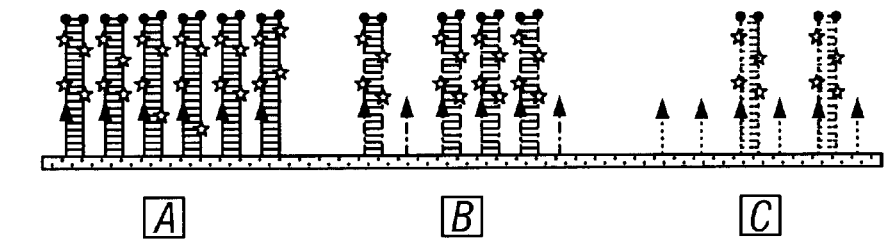
Figure 3A:
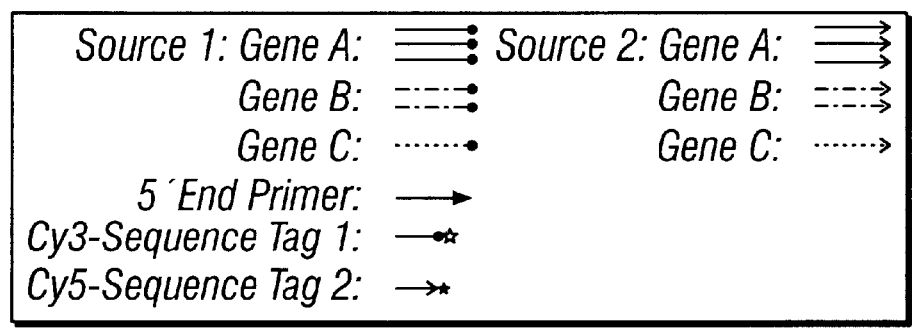
FIGS. 3A–3E depict schematically a solid phase amplification method for amplifying, detecting and comparing target polynucleotides (A, B, C) from two different biological sources, using immobilized primers in combination with differentially labeled sequence tags serving as solution phase primers.
Figure 3A:
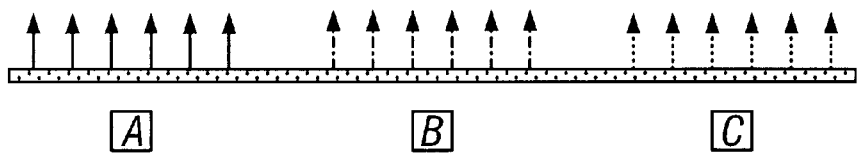
Figure 3B:
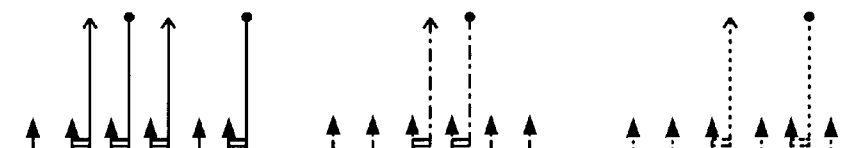
Figure 3C:
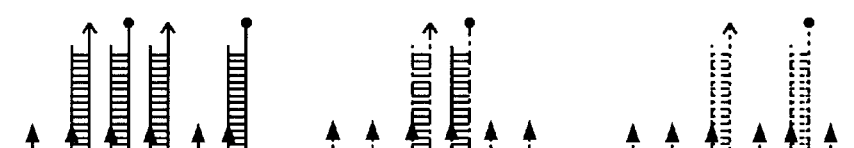
Figure 3D:
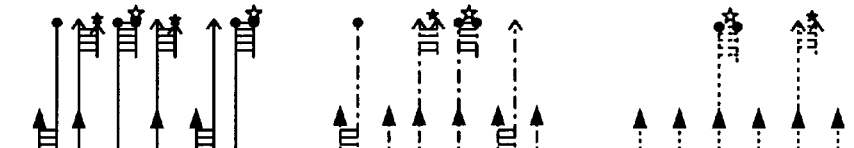
Figure 3E:
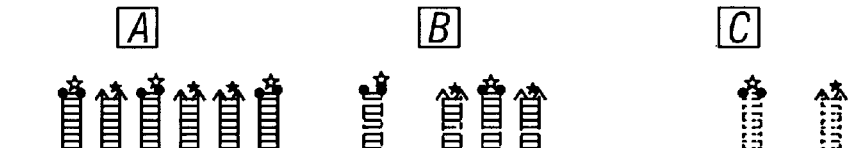

The present invention provides novel methods and compositions for high-throughput fashioned, sensitive yet simple amplification and detection of nucleic acid targets. The invention can be used in various aspects of genome analysis that finds utility in both basic biological research and medical diagnosis and therapeutics.

A "polynucleotide" is a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelators (e.g., metals, radioactive metals, etc.), those containing alkylators, those with modified linkages (e.g., alpha anomeric nucleic acids, etc.), as well as unmodified forms of the polynucleotide.

The term "primer", as used herein, refers to an oligonucleotide which is capable of acting as a point of initiation of polynucleotide synthesis along a complementary strand when placed under conditions in which synthesis of a primer extension product which is complementary to a polynucleotide is catalyzed. Such conditions include the presence of four different nucleotide triphosphates or nucleoside analogs and one or more agents for polymerization such as DNA polymerase and/or reverse transcriptase, in an appropriate buffer ("buffer" includes substituents which are cofactors, or which affect pH, ionic strength, etc.), and at a suitable temperature. A primer must be sufficiently long to prime the synthesis of extension products in the presence of an agent for polymerase. A typical primer contains at least about 5 nucleotides in length of a sequence substantially complementary to the target sequence, but somewhat longer primers are preferred. Usually primers contain about 15–26 nucleotides, but longer primers, up to 35 nucleotides, may also be employed.

A primer will always contain a sequence substantially complementary to the target sequence, that is the specific sequence to be amplified, to which it can anneal. A primer may, optionally, comprise sequences in addition to those that are complementary to the target sequence. Such sequences are preferentially upstream (i.e., at the 5'-end) of the target-complementary sequences in the primer. For example, sequences comprising one or more restriction enzyme recognition sites ("linkers" or "adapters"), when present in a primer upstream of target-complementary sequences, facilitate cloning and subsequent manipulation of an amplification product. Other useful sequences for inclusion in a primer include those complementary to a sequencing primer and those specifying a promoter sequence. The term "promoter sequence" defines a single strand of a nucleic acid sequence that is specifically recognized by an RNA polymerase that binds to a recognized sequence and initiates the process of transcription by which an RNA transcript is produced. In principle, any promoter sequence may be employed for which there is a known and available polymerase that is capable of recognizing the initiation sequence. Known and useful promoters are those that are recognized by certain bacteriophage polymerases, such as bacteriophage T3, T7 or SP6.

As used herein, the term "tag," "sequence tag" or "primer tag sequence" refers to an oligonucleotide with specific nucleic acid sequence that serves to identify a batch of polynucleotides bearing such tags therein. Polynucleotides from the same biological source are covalently tagged with a specific sequence tag so that in subsequent analysis the polynucleotide can be identified according to its source of origin. The sequence tags also serves as primers for nucleic acid amplification reactions.

A "microarray" is a linear or two-dimensional array of preferably discrete regions, each having a defined area, formed on the surface of a solid support. The density of the discrete regions on a microarray is determined by the total numbers of target polynucleotides to be detected on the surface of a single solid phase support, preferably at least about 50/cm$^2$, more preferably at least about 100/cm$^2$, even more preferably at least about 500/cm$^2$, and still more preferably at least about 1,000/cm$^2$. As used herein, a DNA microarray is an array of oligonucleotide primers placed on a chip or other surfaces used to amplify or clone target polynucleotides. Since the position of each particular group of primers in the array is known, the identities of the target polynucleotides can be determined based on their binding to a particular position in the microarray.

A "linker" is a synthetic oligodeoxyribonucleotide which contains a restriction site. A linker may be blunt end-ligated onto the ends of DNA fragments to create restriction sites which can be used in the subsequent cloning of the fragment into a vector molecule.

The term "label" refers to a composition capable of producing a detectable signal indicative of the presence of the target polynucleotide in an assay sample. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

The term "support" refers to conventional supports such as beads, particles, dipsticks, fibers, filters, membranes and silane or silicate supports such as glass slides.

The term "amplify" is used in the broad sense to mean creating an amplification product which may include, for example, additional target molecules, or target-like molecules or molecules complementary to the target molecule, which molecules are created by virtue of the presence of the target molecule in the sample. In the situation where the target is a nucleic acid, an amplification product can be made enzymatically with DNA or RNA polymerases or transcriptases.

As used herein, a "biological sample" refers to a sample of tissue or fluid isolated from an individual, including but not limited to, for example, blood, plasma, serum, spinal fluid, lymph fluid, the external sections of the skin, respiratory, intestinal, and genitourinary tracts, tears, saliva, milk, cells (including but not limited to blood cells), tumors, organs, and also samples of in vitro cell culture constituents.

The term "biological sources" as used herein refers to the sources from which the target polynucleotides are derived from. The source can be of any form of "sample" as described above, including but not limited to, cell, tissue or fluid. "Different biological sources" can refer to different cells/tissues/organs of the same individual, or cells/tissues/organs from different individuals of the same species, or cells/tissues/organs from different species.

In one aspect of the invention, solid phase amplification of target polynucleotides from one biological sample is performed, wherein multiple groups of oligonucleotide primers are immobilized on a solid phase support. In a preferred embodiment, the primers within a group are identical in sequence and are selected or designed to be complementary to a defined sequence of one particular target polynucleotide, capable of hybridizing to the target polynucleotide under appropriate conditions, and suitable as initial primers for nucleic acid synthesis (i.e., chain elongation or extension). Selected primers for each target polynucleotide are immobilized, as a group, onto a solid support at a discrete location. Preferably, the distance between groups is greater than the resolution of detection means to be used for detecting the amplified products. In a preferred embodiment, the primers are immobilized to form a microarray or chip that can be processed and analyzed via automated processing. The immobilized primers are used for solid phase amplification of target polynucleotides under conditions suitable for a nucleic acid amplification means.

According to one aspect of the invention, the initial target polynucleotide is in double-stranded form with a sense strand ("positive strand") and a complementary strand ("negative strand"). Prior to conducting amplification, the target polynucleotide undergoes denaturation, such as thermal denaturation, whereby the two strands are denatured and separated in the reaction solution. Preferably, primers used in the invention are in vast molar excess to the estimated concentration of the target polynucleotides to counteract the renaturation of the two target polynucleotide strands. Alternatively, the initial target polynucleotide is a single-strand, be it a single-stranded DNA or RNA.

In one preferred embodiment of the invention, the nucleic acid amplification is mediated by a polymerase. More preferably, the amplification is performed under conditions suitable for a PCR reaction. As understood by those skilled in the art, a PCR reaction generally involves multiple cycles of annealing-elongating-denaturing steps at varied reaction temperatures, during which multiple copies of nascent strands are synthesized based on the initial target polynucleotides as templates. As the results, the initial target sequences are "amplified" either linearly or exponentially, depending on the condition and restraints of the PCR reaction.

During the PCR reaction according to the present invention, the array of immobilized primers are contacted with target polynucleotides in a reaction mixture, following denaturation if the target polynucleotides are in double-stranded form. Under conditions suitable for annealing, the single stranded target polynucleotide is hybridized to an immobilized single primer which contains sequence complementary to a defined sequence region within the single-stranded target polynucleotide. Under conditions suitable for chain elongation (including but not limited to, the presence of DNA polymerase and free nucleotides dNTPs), each target polynucleotide strand serves as an initial template for synthesis of a nascent complementary strand, which is primed from the 3'-hydroxyl of the annealed primer and extended to the 5'-end of the target template. Following the completion of chain elongation, the reaction condition is changed to allow denaturation, during which the target strand and the nascent strand are separated so that the target strand is released into the sample solution and the nascent strand retained on the solid support via the immobilized primer.

In practicing the present invention, the immobilized single primers can be used alone or, alternatively, in combination with primers in the reaction solution that are complementary to the sequence at the 3'-end of the nascent immobilized strands. Furthermore, the solution phase primers can be either universal primers capable of amplifying all the target polynucleotides or, a pool of specific primers, each of which is specific to a particular target sequence.

In one aspect of the invention, there are no solution phase primers used. Accordingly, the initial amplification reaction as described above produces nascent strands affixed to the solid phase support at each primer site, either as a single strand or annealed with an initial target polynucleotide strand, depending upon whether or not a denaturation step is introduced after elongation. And the presence of these nascent strands can be detected by appropriate detection means as further described below.

In another aspect of the invention, solution phase primers are used in combination with the solid phase immobilized primers for the amplification of the multiple target polynucleotides. Subsequent to the initial amplification reaction, another round of amplification reaction is performed, during which the previously formed nascent strand complementary at its 3'-end to the solution phase primers will anneal to the solution phase primers and serve as a template for a subsequent synthesis of a second nascent strand substantially identical to the target polynucleotide. As the result, a double-stranded nascent polynucleotide can be formed and affixed on the solid phase support at each primer site.

Examples of the solid phase amplification approach of the invention are depicted in FIGS. 1 and 2:

FIG. 1 depicts amplification and detection of three target genes, A, B and C, on a solid phase support having three sets of immobilized 5'-end primers, each set specific to a particular target gene. No additional primers are present in the solution. In 1A, the array of immobilized primers specific to genes A, B and C are depicted with closed arrows. In 1B, single stranded target polypeptides hybridize to the immobilized 5'-end primers at their complementary sequence regions under conditions for annealing. Then in 1C, conditions are shifted for elongation, during which the 5'-end primers serve as initiation sites for synthesis of nascent strands using the target polynucleotides as templates. Nascent strands are synthesized with a label, biotin-dCTP, incorporated therein so that the nascent strands can later be detected. At the completion of elongation, the conditions are shifted to denaturation, during which the original target template strands are released from the array into the solution and the labeled nascent single strands are covalently linked to the support via the immobilized 5'-end primers. In 1D, a second round of annealing occurs so that the target template strands hybridize to additional immobilized primers for further amplification. 1E shows the resulting amplification products at immobilized primer sites, some are single stranded, biotin-labeled polynucleotide and others are double stranded because the target templates remain annealed with the nascent strands without denaturation. Because the immobilized primers are in vast molar excess to the estimated concentration of the target templates, it results in the existence of both single and double stranded amplification products even without the presence of solution phase primers.

FIG. 2 depicts amplification and detection of target genes (A, B and C) with both immobilized specific 5'-end primers and solution phase 3'-end primers. 3'-primers can be universal primers such as poly-dT for binding to polyadenylated mRNA templates. 2A–2C essentially correspond to 1A–1C in illustrating a first round of PCR at each immobilized 5'-end primer site and the resulting single stranded nascent strands that can be detected with the incorporated biotin-labels. After denaturation, the target templates are separated from the nascent strands and released into the solution. 2D depicts a second round PCR during with each nascent strands serve as templates for another nascent strand synthesis initiated from the solution phase universal primers. Meanwhile, the original target templates hybridize to additional immobilized 5'-primer sites for further amplification. The results are double-stranded amplification products on the immobilized primer sites, with each strand being biotinylated, as shown in 2E.

The solid phase amplification methods of the invention can be used to detect and compare gene expressions in different biological sources. In this aspect, the immobilized primers are used in combination with solution phase primers for the conduction of amplification reactions. According to one embodiment, different sources can be different tissues or cells of the same subject. Alternatively, different sources are comparable tissues of two or more different subjects of same species, e.g., one from a healthy control, and another from a patient. In yet another embodiment, different sources are of two or more different species or different animals, such as one of human and another of mouse.

The differential analysis of gene expression according to the invention is performed essentially by amplifying the target polynucleotides from different biological sources together on the solid phase array of primers. In this embodiment the batch of initial target polynucleotides from each source are differentially tagged with an oligonucleotide sequence, so that the end amplification products bear such sequence tags, indicating the source of the initial targets. By detecting and comparing the amplification products labeled with "source tags," the presence and relative abundance of the target polynucleotides in different sources can be determined and compared.

As an illustration of this embodiment of the invention, the original target polynucleotides from different biological sources are total mRNAs expressed therein. Methods and materials that are known in the art are used to isolate total mRNAs from each source. The total pool of isolated mRNA from each biological source is then used to prepare a batch of specifically tagged cDNA that are to be used as "target polynucleotide templates" for subsequent amplification. In one embodiment, each batch of the reverse-transcribed cDNAs are tagged with a specific sequence tag at their 3'-ends. The specific sequence tag is not present in any of the unmodified target polynucleotides. For example, if the target polynucleotides to be detected are from human cells/tissues, the sequence tag can be derived from a bacteria or viral genome and the sequence does not anneal under hybridization/amplification conditions with the human sequences that are transcribed into mRNA. In this way, the sequence tags from one batch will not cause artifactual amplification of another batch due to cross-hybridization.

Furthermore, the sequence tag for each batch of cDNA targets is different from that for another batch of cDNA targets so that they can be compared. The sequence tag can be introduced into the reverse-transcribed cDNA by using a specially designed primer for reverse transcription. For example, a primer can have a poly-dT portion at its 3'-end and a bacterial SP6 sequence at its 5'-end. During reverse transcription, mRNAs serve as template for a cDNA synthesis initiated from the 5'-end of the poly-dT portion that anneals with the poly-A tail of the mRNA templates. The resulting cDNA products then have at their 5'-end a SP6 "sequence tag," which is unique to this batch of cDNAs. Similarly, a different batch of cDNAs from another source can be "tagged" with a different sequence tag, such as a bacterial T7 sequence.

The two batches of cDNAs that are differentially tagged with, for example, SP6 and T7 are mixed together for amplification and detection. Present in the amplification reaction mixture are free SP6 and T7 sequence tags that are differentially labeled. For example, the two sequence tags can be labeled either with two different fluorescent dyes (e.g., one red dye and one green dye) for direct detection or, alternatively, with two chemical moieties (e.g., one biotin and one digoxigenin) for subsequent color detection. It is important that the labels do not occur at the 3'-end of the sequence tags so that the sequence tags can latter serve as primers in amplification reaction.

A preferred amplification means for the invention is PCR reaction. The mixture of two differentially tagged batches of cDNAs are contacted with an solid phase array of multiple groups of specific primers, with each group corresponding to a particular target cDNA as described above. In the initial round of PCR, the immobilized primers anneal with target polynucleotides from both sources and synthesize a nascent complementary strand under conditions sufficient for chain elongation. The nascent complementary strand spans through the target sequence region and contains at its 3'-end a sequence complementary to the sequence tag at the end of the target cDNA template. For example, a first nascent strand has a 3'-end complementary to the SP6 sequence if it was amplified on a SP6-tagged cDNA template from source 1; and a second nascent strand has a 3'-end complementary to the T7 sequence if it was amplified on a T7-tagged cDNA template from source 2. Thus, each nascent strand immobilized on the solid phase array "inherits" the sequence tag specific to its source.

In the subsequent rounds of PCR, the first set of nascent strands tagged for different sources serve as templates for the synthesis of a second set of nascent strands. This time, the initial primers of the PCR are the differentially labeled free sequence tags in solution, such as fluorescein-labeled SP6 primers and lissamine-labeled T7 primers. Accordingly, the second set of nascent strands extended from the labeled sequence tags are differentially labeled corresponding to the original sources of the target cDNA templates in the original round of PCR reaction. After washing off the unbound reagents and original templates without denaturation, each immobilized primer site will have a double stranded polynucleotide having on one strand a label indicating the original biological source. As such, the final detection of different labels will reveal the presence and abundance of particular target polynucleotides in different biological sources.

It is understood by those skilled in the art that to practice the invention, one does not need to measure the exact quantity of gene expression from each biological source, although such accurate measurement is possible. Rather, the invention provides an approach for the comparative analysis of gene expression in different sources. The detection of the different labels, at each primer spot on an array are used to determine the ratio, and in turn the relative abundance, of each target polynucleotide from the different biological sources.

An example of the differential expression analysis of different biological sources is illustrated in FIG. 3:

FIG. 3 depicts amplification and detection of target genes from two different samples, with each target gene being tagged with a sample-specific sequence tag. The amplification reaction is conducted in the presence of solution phased, differentially labeled sequence tags, for example, Cy3-sequence tag 1 and Cy5-sequence tag 2. In 3A, 5-end primers specific to each gene are immobilized in groups on a solid support. In 3B, the target strands that have previously been tagged with sequence tags on their 5'-end are annealed to the immobilized 5'-end primers and serve as templates for a PCR amplification. In 3C, nascent strands complementary to the target templates are initiated from each immobilized primer site, and are spanned through the target sequence to the 3'-end that is complementary to the sequence tags. As such, each nascent strand is also tagged with the complementary tag sequences. At the completion of the first round of amplification, the original target templates are released from the nascent strands during a denaturation. Then 3D depicts a second round of PCR, during which each immobilized nascent strand serve as a template and the solution phase, Cy3- or Cy5-labeled sequence tag serves as a primer for the synthesis of another nascent strand. As the results, each of the new strands will bear either Cy3 or Cy5 label, depending on the sample origin from which the corresponding target gene comes. Also in 3D, the original target templates anneal to additional immobilized 5'-end primer sites to start a new round of amplification. At the completion of the second round of PCR, no denaturation occurs so that the Cy3 or Cy5-labeled nascent strands remain annealed to the immobilized nascent strands. Therefore, as shown in 3E, the immobilized amplification products can be detected for the presence of either Cy3 or Cy5, which are indicative of the sources of the original target genes.

The differential expression analysis of the present invention has utility in a variety of aspects of biological research as well as clinical applications. For example, the expression patterns of particular genes of interest in multiple systems can be compared within one sample mixture to minimize the deviation. It enables a comparison of expression levels of certain genes between, for example, different species and thus to assess the functionality of the genes of interest. Also, the invention is useful in clinical diagnosis of certain genetic defects of a diseased patient by comparing the expression level of the target genes to a healthy individual. Moreover, using the present invention, gene expression levels in different cells/tissues/organisms can be compared to assess certain genes' roles in particular biological pathways.

The amplification methods described above can be used for a high throughput assay of multiple target polynucleotides on a single solid phase support. Multiple groups of primers, either in single form or in pairs, are immobilized onto a solid phase support to form a microarray with predetermined pattern. Each group of primers correspond to a particular target polynucleotide and occupies a discrete position within the microarray. When a sample containing or suspected of containing multiple target polynucleotides is in contact with the microarray under reaction conditions suitable for PCR reactions as described above, each target polynucleotide will be amplified and affixed at a discrete position with the microarray having corresponding primers immobilized thereto.

According to the invention, the number of potential target polynucleotides is limited only by the available technology for producing and analyzing small dense microarrays. For example, using known technologies up to about 100,000 polynucleotides may be analyzed on a single solid support by providing up to about 100,000 different populations of primer pairs at discrete locations on the solid support, and contacting the support with a PCR solution and a sample comprising at least one copy of the target polynucleotides that the primers are designed to detect.

Methods and Materials

1. Target Polynucleotides

For the purpose of the invention, target polynucleotides can be double stranded DNA, single stranded DNA, or RNA. Examples of target polynucleotide include, but are not limited to, genomic DNA, cDNA, mRNA, mitochondria DNA, viral DNA, amplified DNA, and viral RNA. Double-stranded target polynucleotides undergo denaturation at the beginning of the amplification reactions to provide single-stranded templates.

mRNA target polynucleotides can be directly used as templates for amplification mediated by reverse transcriptase. Following the completion of chain elongation originating at each immobilized primer site, the hybridized RNA template strand can be destroyed by, for example, RNAse H, leaving the nascent complementary DNA strand affixed to the solid phase support. If a second primer (either specific or universal) is present in the solution phase, the first nascent cDNA strand will serve as a template for synthesizing another nascent strand, thereby forming a double-stranded nascent DNA molecule at each immobilized primer site or binding two immobilized primers.

Alternatively, mRNA target polynucleotides in a sample can be first reverse-transcribed into complementary DNAs which in turn serve as initial templates for the solid phase PCR reactions of the invention. The reverse transcription can be initiated from, for example, a poly-dT universal primer that can also be used as the universal primer in solution phase for a PCR amplification reaction according to the invention. A poly-dT initiated cDNA product will anneal at its 3'-end to the specific primer immobilized on the solid phase support and serves as template for subsequent synthesis of a nascent complementary strand having at its 3'-end a poly-A sequence. Following a denaturation step, the single immobilized nascent strand is capable of hybridizing to a poly-dT universal primer in the solution phase and serving as template for subsequent round of PCR amplification and formation of double-stranded nascent polynucleotides that are affixed to the solid phase support.

Multiple polynucleotides of the invention can be from one single biological source or, alternatively, from multiple biological sources such as different species or tissues. For example, a population of target polynucleotides isolated from a healthy individual can be mixed in one PCR reaction with another population of target polynucleotides isolated from a patient with a disease of interest, under conditions that would allow distinguishing amplified products of the two sources by detection methods known in the art, as described in detail above. Therefore, the present invention can be used for cross-species comparative analysis of target polynucleotides.

2. Oligonucleotide Primers

The invention provides a prepared solid support comprising separate, immobilized groups of oligonucleotide primers. Each primer is suitable for conducting an amplification for a particular target polynucleotide. The primers can thus be selected or designed based on a region of known sequence in the target polynucleotide, using, for example, a standard PCR primer selection program such as Primer3 from Massachusetts Institute of Technology (MIT).

The solid phase support can provide an areas of about 5 to about 100 square micrometers, on which up to about 100,000 groups of single primers can be immobilized in discrete areas according to a predetermined pattern. The prepared solid support can have an associated written or electronic record of the sequence of the primer or primer pairs at any given location on the support, and thus the location on the support of an amplified target can be identified as well.

The number of primers within each group corresponding to a particular target nucleotide can be determined and limited by the needs of the subsequent planned amplification reaction on the microarray. Thus, for example, the number of primers deemed necessary for conducting an PCR at a specific site on the microarray, given especially the reaction volume and expected number of target template polynucleotide molecules, and the proposed number of cycles of PCR, will help determine exactly how much oligonucleotide primer copies to apply as a group at each location on the support to ensure successful reactions. Preferably, the amounts of primers (i.e. primer molecule numbers or primer concentration) will be about the same at each provided location on a given solid support (e.g. in a DNA microarray format having from 1000, to 10,000, up to about 100,000 populations of primers to amplify or detect up to about 100,000 target polynucleotides).

The solid support can be prepared with primer sequences for a particular application based on the polynucleotides to be detected. The oligonucleotide primers can be of any length suitable for a particular PCR, especially considering the sequence and quality of the target polynucleotides to be amplified. As an example, the primers can be from about 4 to about 30 nucleotides in length.

It is understood that a nucleic acid primer of the present invention may contain minor deletions, additions and/or substitutions of nucleic acid bases, to the extent that such alterations do not negatively affect the yield or product obtained to a significant degree.

Oligonucleotide primers can include the naturally-occurring heterocyclic bases normally found in nucleic acids (uracil, cytosine, thymine, adenine and guanine), as well as modified bases and base analogues. Any modified base or base analogue compatible with hybridization of the primer to a target sequence is useful in the practice of the invention. The sugar or glycoside portion of the primer can comprise deoxyribose, ribose, and/or modified forms of these sugars, such as, for example, 2'-O-alkyl ribose. In a preferred embodiment, the sugar moiety is 2'-deoxyribose; however, any sugar moiety that is compatible with the ability of the primer to hybridize to a target sequence can be used.

In one embodiment, the nucleoside units of the primer are linked by a phosphodiester backbone, as is well known in the art. In additional embodiments, internucleoside linkages can include any linkage known to one of skill in the art that is compatible with specific hybridization of the primer including, but not limited to phosphorothioate, methylphosphonate, sulfamate (e.g., U.S. Pat. No. 5,470,967) and polyamide (i.e., peptide nucleic acids). Peptide nucleic acids are described in Nielsen et al. (1991) *Science* 254: 1497–1500; U.S. Pat. No. 5,714,331; and Nielsen (1999) *Curr. Opin. Biotechnol.* 10:71–75.

In certain embodiments, the primer can be a chimeric molecule; i.e., can comprise more than one type of base or sugar subunit, and/or the linkages can be of more than one type within the same primer. The primer can comprise a moiety to facilitate hybridization to its target sequence, as is known in the art, for example, by incorporating intercalators and/or minor groove binders.

Variations of the bases, sugars, and internucleoside backbone, as well as the presence of any pendant group on the primer, will be compatible with the ability of the primer to bind, in a sequence-specific fashion, with its target sequence. A large number of structural modifications, both known and to be developed, are possible within these bounds. Moreover, synthetic methods for preparing the various heterocyclic bases, sugars, nucleosides and nucleotides which form the primer, and preparation of oligonucleotides of specific predetermined sequence, are well-developed and known in the art. A preferred method for oligonucleotide synthesis incorporates the teaching of U.S. Pat. No. 5,419,966.

The oligonucleotide primers can be designed with any special additional moieties or sequences that will aid and facilitate a particular PCR or subsequent manipulations, e.g. isolation of the amplified target polynucleotides. For example, a primer can comprise sequences in addition to those that are complementary to the target sequence. Such sequences are normally upstream (i.e., to the 5'-side) of the target-complementary sequences in the primer. For example, sequences comprising one or more restriction enzyme recognition sites (so-called "linkers" or "adapters"), when present in a primer upstream of target-complementary sequences, facilitate cloning and subsequent manipulation of an amplification product. Other useful sequences for inclusion in a primer include those complementary to a sequencing primer and those specifying a promoter for a bacteriophage RNA polymerase, such as T3 RNA polymerase, T7 RNA polymerase and SP6 RNA polymerase.

Where solution phase primers are also used to conduct the PCR amplification, the solution phase primers can be universal primers. Different universal primers can be used for tissues or specie samples to be compared. These different primers can be differentially labeled (e.g. green for one and red for another) so that during the detection, targets that are from one species or tissue sample can be distinguished from the corresponding targets from another species or tissue sample.

Furthermore, the oligonucleotide primers of the invention can be designed to detect or clone mutant polynucleotides that contain specific nucleotide mutations as compared to their wild type counterparts. The primers can be designed based on the sequence of the wild type polynucleotides but differ at the last nucleotide of the 3'-end. As such, these 3'-end substituted primers would not be able to bind and PCR amplify the wild type target polynucleotides. In stead, they would recognize and amplify those mutant ones having a sequence mutation that match the nucleotide substitution. By using an array of 3'-end substituted primers spanning a region of interest, one is able to detect mutations within the region.

3. Solid Phase Support

The solid phase support of the present invention can be of any solid materials and structures suitable for supporting nucleotide hybridization and synthesis. Preferably, the solid phase support comprises at least one substantially rigid surface on which the primers can be immobilized and the PCR reaction performed. The solid phase support can be made of, for example, glass, synthetic polymer, plastic, hard non-mesh nylon or ceramic. Other suitable solid support materials are known and readily available to those of skill in the art. The size of the solid support can be any of the standard microarray sizes, useful for DNA microarray technology, and the size may be tailored to fit the particular machine being used to conduct a reaction of the invention. Methods and materials for derivatization of solid phase supports for the purpose of immobilizing oligonucleotides are known to those skill in the art and described in, for example, U.S. Pat. No. 5,919,523, the disclosure of which is incorporated herein by reference.

The solid support can be provided in or be part of a fluid containing vessel. For example, the solid support can be placed in a chamber with sides that create a seal along the edge of the solid support so as to contain the polymerase chain reaction (PCR) on the support. In a specific example the chamber can have walls on each side of a rectangular support to ensure that the PCR mixture remains on the support and also to make the entire surface useful for providing the primers.

4. Primer Immobilization

The oligonucleotide primers of the invention are affixed, immobilized, provided, and/or applied to the surface of the solid support using any available means to fix, immobilize, provide and/or apply the oligonucleotides at a particular location on the solid support. For example, photolithography (Affymetrix, Santa Clara, Calif.) can be used to apply the oligonucleotide primers at particular position on a chip or solid support, as described in the U.S. patents, U.S. Pat. No. 5,919,523, U.S. Pat. No. 5,837,832, U.S. Pat. No. 5,831,070, and U.S. Pat. No. 5,770,722, which are incorporated herein by reference. The oligonucleotide primers may also be applied to a solid support as described in Brown and Shalon, U.S. Pat. No. 5,807,522 (1998). Additionally, the primers may be applied to a solid support using a robotic system, such as one manufactured by Genetic MicroSystems (Woburn, Mass.), GeneMachines (San Carlos, Calif.) or Cartesian Technologies (Irvine, Calif.).

5. PCR Reaction

In practicing the invention, a reaction mixture comprising the appropriate target polynucleotides mixed with the reagents necessary for conducting the polymerase chain reaction (PCR) are placed in contact with each immobilized primer pair or single primer population on the solid support. The appropriate target polynucleotides can be double stranded DNA, single stranded cDNA generated by reverse transcription of RNA templates, or mRNA population. The reaction mixture contains an enzyme for facilitating the synthesis of a polynucleotide strand complementary to a target strand. Suitable polymerases include thermostable polymerase enzymes, such as Taq DNA polymerase, TthI DNA polymerase, Tne DNA polymerase, Tma DNA polymerase, Pfu DNA polymerase, Vent DNA polymerase or any other thermostable DNA polymerase. The reaction mixture can also contain a label molecule capable of being incorporated into the nascent strands during polymerase chain reaction so that the amplified products can be detected on the solid support after the PCR. The label can be detected directly or indirectly according to methods well known in the art. Suitable labels for direct detection can be any fluorescent molecules such as fluorescein isothiocyanate, Texas red or rhodamine. Molecules facilitating indirect detection, such as biotin or digoxigenin, can also be incorporated into the nascent strands during the PCR. Biotin can be subsequently detected by binding to a labeled streptavidin or a labeled anti-biotin antibody. Likewise, incorporated digoxigenin can be detected by a labeled or unlabeled anti-digoxigenin antibody, and the unlabeled anti-digoxigenin antibody can be detected by binding a labeled anti-anti-digoxigenin antibody.

After the reagents for conducting the PCR contact the immobilized primers on the microarray, the microarray is placed in conditions that facilitate the PCR to take place, using for example an automated system such as an in situ PCR machine. The reaction conditions for the PCR procedure can be as recommended by the in situ PCR machine manual, and may be varied as appropriate given the nature of the templates being used or any other difficulties anticipated with the primers and template hybridization. Temperatures and number of cycles can be selected as recommended and as appropriate given the primer selection and the template sequences, and any other relevant factors. The in situ-type PCR reactions on the microarrays can be conducted essentially as described in e.g. Embretson et al, *Nature* 362:359–362 (1993); Gosden et al, *BioTechniques* 15(1):78–80 (1993); Heniford et al *Nuc. Acid Res.* 21(14): 3159–3166 (1993); Long et al, *Histochemistry* 99:151–162 (1993); Nuovo et al, *PCR Methods and Applications* 2(4): 305–312 (1993); Patterson et al *Science* 260:976–979 (1993).

6. Labeling and Detection

The PCR methods of the invention provide for detection of multiple target polynucleotides in a sample. After the PCR is completed in the presence of appropriate labeling reagents, the amplified and labeled target polynucleotides can be detected at each of the original primer locations on the microarray. Detecting the amplified or labeled target polynucleotides can be conducted by standard methods used to detect the labeled sequences, including for example, detecting labels that have been incorporated into the amplified or newly synthesized DNA strands. Thus, for example fluorescent labels or radiolabels can be detected directly. Other labeling techniques may require that a label such as biotin or digoxigenin that is incorporated into the DNA during strand synthesis be detected by an antibody or other binding molecule (e.g. streptavidin) that is either labeled or which can bind a labeled molecule itself, for example, a labeled molecule can be e.g. an anti-streptavidin antibody or anti-digoxigenin antibody conjugated to either a fluorescent molecule (e.g. fluorescein isothiocyanate, Texas red and rhodamine), or conjugated to an enzymatically activatable molecule. Whatever the label on the newly synthesized molecules, and whether the label is directly in the DNA or conjugated to a molecule that binds the DNA (or binds a molecule that binds the DNA), the labels (e.g. fluorescent, enzymatic, chemiluminescent, or calorimetric) can be detected by a laser scanner or a CCD camera, or X-ray film, depending on the label, or other appropriate means for detecting a particular label.

The target polynucleotides can be detected by using labeled nucleotides (e.g. dNTP-fluorescent label for direct labeling; dNTP-biotin or dNTP-digoxigenin for indirect labeling) are incorporated into amplified DNA during the PCR. For indirectly labeled DNA, the detection is carried out by fluorescence or other enzyme conjugated streptavidin or anti-digoxigenin antibodies. The PCR method employs detection of the polynucleotides by detecting incorporated label in the newly synthesized complements to the polynucleotide targets. For this purpose, any label that can be incorporated into DNA as it is synthesized can be used, e.g. fluoro-dNTP, biotin-dNTP, or digoxigenin-dNTP, as described above and are known in the art. PCR amplification conducted using one or more universal primers in solution provides the option to detect the amplified targets at locations on the solid support by detecting the universal primers. Thus, where more than one universal primer is used, target strands from different sources can be differentially detected on the solid support.

In a differential expression system, amplification products derived from different biological sources can be detected by differentially labeling the amplified strands based on their origins, as described in the section under "C. Comparing Differential Expression of Genes from Different Biological Sources." In one aspect, the detection methods used herein are different from the detection method for single-source targets, in that the differential labels (e.g., red dye and green dye) are pre-incorporated on the primer tags in solution, rather than being incorporated into the nascent strands during the amplification. Alternatively, a third label can also be incorporated into the nascent strand during amplification, in addition to the differential labels, so that the overall sensitivity for differential expression comparison is enhanced.

7. Detection Kits

The invention provides kits for practicing the methods of the invention. The kit can include, e.g. the materials and reagents for detecting a plurality of target polynucleotides that are otherwise difficult to detect on a solid support. The kit can include e.g. a solid support, oligonucleotide primers for a specific set of target polynucleotides, polymerase chain reaction reagents and components, e.g. enzymes for DNA synthesis, labeling materials, and other buffers and reagents for washing. The kit may also include instructions for use of the kit to amplify specific targets on a solid support. Where the kit contains a prepared solid support having a set of primers already fixed on the solid support, e.g. for amplifying a particular set of target polynucleotides, the design and construction of such a prepared solid support is described above. Such solid supports can be custom-made for individual kits depending on the target polynucleotides the customer desires to detect. The kit also includes reagents necessary for conducting a PCR on a solid support, for example using an in situ-type or solid phase type PCR procedure where the support is capable of PCR amplification using an in situ-type PCR machine. The support can be contacted with the reagents for PCR. A sample potentially containing multiple target polynucleotides is added to the PCR reagent mixture before the reaction. The PCR reagents include the usual PCR buffers, a thermostable polymerase (e.g. Taq DNA polymerase), nucleotides (e.g. dNTPs), and other components and labeling molecules (e.g. for direct or indirect labeling as described above). The solid support provides the affixed primers in designated locations on the solid support. For conducting the PCR, the support with the immobilized primers is contacted with reagents for conducting PCR and the target polynucleotide templates in a reaction mix and the subjected to PCR (e.g. in situ type or solid phase type PCR) conditions. The instructions for use of the kits can include, e.g. such details for the procedure as indicated in the description of the methods above. The kits can be assembled to support practice of the PCR amplification method using immobilized primers alone or, alternatively, together with solution phase primers.

EXAMPLES

Example 1

Amplification of Four Target DNA Templates on Microarrays

Four cDNA target polynucleotides, human G3PDH, PKC-α, c-Raf, and Cyclin A, were selected for detection by amplification on a microarray, either by a symmetric PCR in which both members of a primer pair are immobilized onto the support, or by an asymmetric PCR in which one member of the primer pair is immobilized and another member is in solution.

a. Symmetric Amplification of G3PDH

Based on the presumed or deduced sequences of these target polynucleotides, populations of primer pairs were designed and synthesized for each of the four targets. The primers were synthesized with a 5'-end modification of amine to aid in affixing the primers to the solid support. The primers were spotted in pairs or as single primers, at different concentrations, on a silanated glass slide purchased from Sigma Chemicals (St. Louis, Mo.).

The silanated slides with the provided primers were hydrated overnight in saturated NaCl chamber at room temperature. The hydrated slides were rinsed with 4×SSC for 5 minutes and then washed with water. The slides were blocked with SurModics (Madison, Wis.) blocking solution (with 0.1% SDS) for 15 minutes at 50° C., and then rinsed twice with water and air-dried. The slides were then ready for use.

The PCR reaction solution was prepared to give a final concentration at 200 µM each dATP, dGTP, and dTTP; 100 µM dCTP and 100 µM Biotin-14-dCTP. The reaction solution also contains 1× Taq reaction buffer (with 1.5 mM $MgCl_2$); human G3PDH gene plasmids as DNA templates (100 ng phagemid DNA or 500 ng ss-cDNA library) and 2.5 units of Taq enzyme. 70 µl reaction solutions was generated as follows:

| | |
|---|---|
| 7 µl | 2 mM d3TP (dATP, dGTP, and dTTP) |
| 12.5 µl | 0.4 mm dCTP |
| 12.5 µl | 0.4 mM Biotin-14-dCTP |
| 7 µl | 10X reaction buffer (w/15 mM MgCl$_2$) |
| 5 µl | DNA template |
| 25.5 µl | water |
| 0.5 µl | 5 units/µl of Taq DNA Polymerase for total volume of 70 µl. |

A HyBaid chamber (Franklin, Mass.) was placed on the slide to keep the arrayed locations in the center, and the reaction solution was transferred to the chamber and sealed with a plastic cover. The PCR machine was pre-warmed, and the following cycling protocol was applied:

| | | |
|---|---|---|
| beginning | 94° C. | 5 minutes |
| main cycle: (steps 1–3) repeat 35X | | |
| 1 | 94° C. | 30 seconds |
| 2 | 55° C. | 30 seconds |
| 3 | 72° C. | 30 seconds |
| final extension | 72° C. | 7 minutes |
| end | 4° C. | hold |

After the PCR was completed, the slide was blocked with a digoxigenin-blocking solution from Boehringer Mannheim (Indianapolis, Ind.) for 30 minutes at room temperature. The slide was stained with streptavidin (5 µg/µl) (1:250 dilution in digoxigenin-blocking solution) for 30 minutes at room temperature with gentle shaking. Digoxigenin-washing buffer was used to wash the slide for 15 minutes at room temperature, twice. The slide was blocked with digoxigenin-blocking solution for 30 minutes at room temperature.

The slide was incubated with the first antibody (rabbit anti-streptavidin) diluted 1:100 in digoxigenin-blocking solution for 1 hour at room temperature. The slide was washed with digoxigenin-washing buffer for 15 minutes at room temperature, twice. The slide was incubated with the second antibody (Cy3 conjugated goat anti-rabbit antibody) diluted 1:100 in digoxigenin-blocking solution for 30 minutes at room temperature. The slide was washed with Digoxigenin-washing buffer for 15 minutes at room temperature, twice. The slide was scanned with green beam from Genetic MicroSystem, GMS418.

Figure 4A:
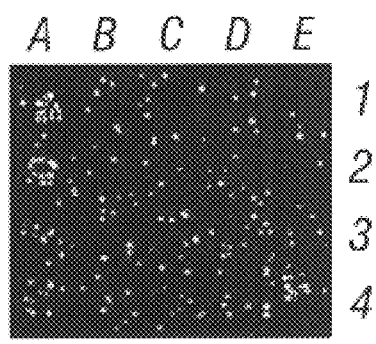
FIGS. 4A–4C show the results of solid phase amplification experiments using four target cDNA as templates.

The results of the symmetric PCR is shown in FIG. 4A. The illuminated spots indicates successful amplification of the hu G3PDH template at the spots wherein human G3PDH primers are immobilized. In contrast, no detection of the target human G3PDH template is seen at any spots where other non-human G3PDH primers were immobilized.

b. Asymmetric Amplification of hu G3PDH

An asymmetric PCR reaction was performed using sets of primers for each of the four target cDNAs, hu G3PDH, PKC-α, c-Raf, and Cyclin A. Each spot on the microarray contains a set of primers specific for a target cDNA at defined concentration as marked in FIG. 4B. In addition to the immobilized primers, hu G3PDH antisense primers were also included in the reaction solution, at 25 pmol. PCR amplification using 1 pg hu G3PDH cDNA as template was conducted under conditions as described above.

Figure 4B:
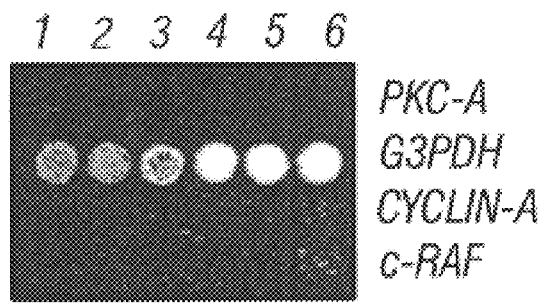

The results of asymmetric PCR of hu G3PDH cDNA is shown in FIG. 4B. The spotting primer concentrations, from columns 1 to 6, are 3.125, 6.25, 12.5, 25, 50 and 100 pmol/µl respectively. The illuminated spots indicate that only the amplification products of hu G3PDH can only be detected in spots containing hu G3PDH primers, suggesting strong specificity of the assay. Furthermore, the resolution of the asymmetric PCR results appears to be higher than the symmetric PCR results shown in FIG. 2A, suggesting a better sensitivity with the asymmetric methods.

c. Asymmetric Amplification of Four Target cDNAs on One Microarray

The asymmetric methods of the invention was further tested for detecting multiple target polynucleotides on one single microarray.

The microarray and the primers thereon were the same as in 1b, with each spot containing a set of single primers specific to a target cDNA and having determined concentration. The reaction solution contained, at 25 pMol each, antisense strand primers for each of the four target cDNAs. The reaction solution also contained each of the four cDNAs as templates for PCR amplification. The PCR reaction was conducted as described in Example 1a.

Figure 4C:
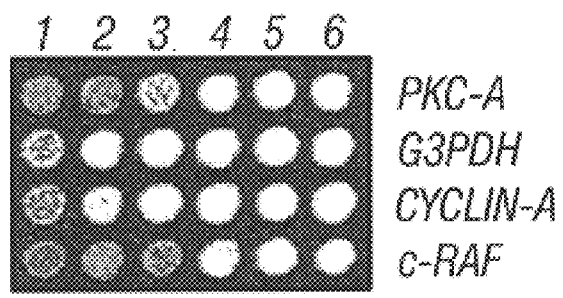

The results as shown in FIG. 4C indicate that all the target templates were successfully amplified, even at the spots with the lowest concentration of primers.

Example 2

Solid Phase Amplification of RNA Targets

In this example, the asymmetric PCR method was tested for detecting mRNA expressions in a biological sample.

5 µg mRNA was isolated from OVC 1.1 cells and used for reverse-transcription of single-strand cDNA. The SuperScript II kit (Life Technology Inc.) was used to carry out the reverse transcription reaction. 0.5 µg prepared cDNA was used as template to run an asymmetric PCR with 25 pMol universal primer (Uni-1) in the reaction solution, and various concentrations of specific primers for four target genes, hu G3PDH, PKC-α, cyclin-A and c-Raf, were immobilized on different spots of a microarray. The PCR reaction was conducted according to conditions and procedures as described in Example 1(a) above.

Figure 5:
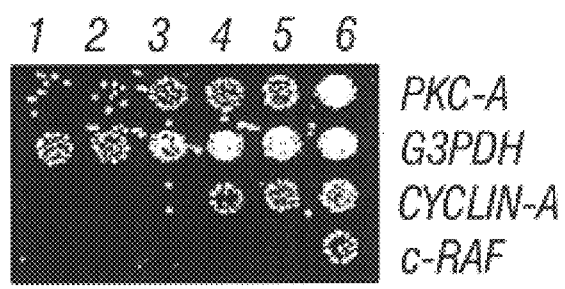
FIG. 5 shows the result of solid phase amplification of target mRNA.

The results are shown in FIG. 5. The expression patterns of the four target genes show different abundance of the expression, with hu G3PDH the most abundant and c-Raf the least.

Example 3

Signal Enhancement by Solid Phase Amplification Prior to Hybridization

In this example, the signal generated by hybridization alone was compared to the signal generated when solid phase amplification by PCR was carried out prior to hybridization. As illustrated in FIG. 6, signals from gene expression analyses of ovarian carcinoma cell line OVC 1.1 and fetal brain were compared with and without performing solid phase PCR prior to hybridization on microarrays.

Figure 6A:
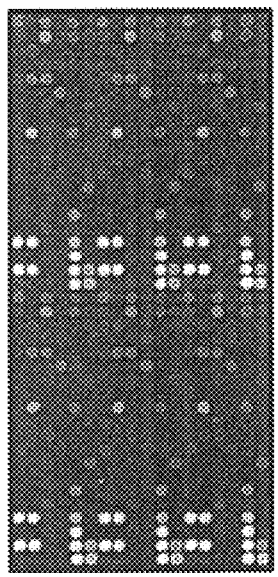
Figure 6B:
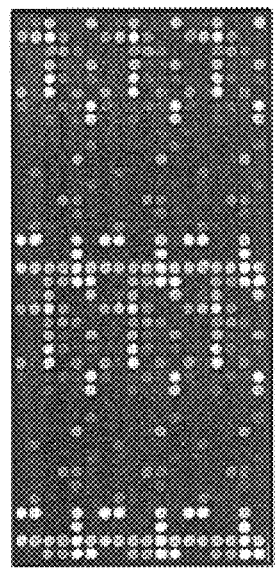
FIG. 6B illustrates the results of hybridization following an solid phase PCR reaction.

FIGS. 6A–6B illustrate a cDNA microarray containing array elements from OVC1.1 cells hybridized with a fluorescent probe prepared from total mRNA by enzymatic labeling according to standard methods. (see, Schena M., and Davis R. W., (1998). genes, Genomes and Chips. in DNA Microarrays: A Practical Approach (ed. M. Schena), Oxford University Press, Oxford, U.K.). FIG. 6A illustrates the hybridization signal following standard protocols, whereas FIG. 6B illustrates the results of hybridization following an solid phase PCR reaction conducted according to conditions and procedures as described in Example 1(a) above.

Figure 6C:
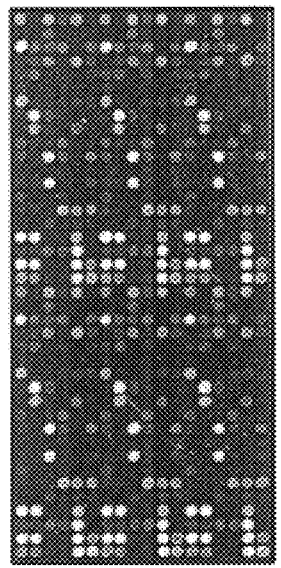
Figure 6D:
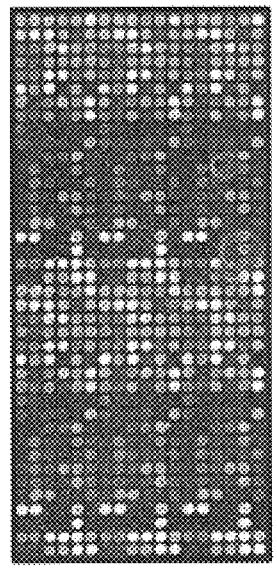
FIG. 6D illustrates the results of hybridization following an solid phase PCR reaction.

The results of another experiment along the same lines is shown in FIGS. 6C–6D. FIG. 6C illustrates the signal following hybridization of fluorescent labeled cellular mRNA probe to a microarray comprising fetal brain cDNA target, whereas FIG. 6D illustrates the results of hybridization following an solid phase PCR reaction according to the present invention.

Example 4

Specificity of Hybridization Signal Following Solid Phase Amplification

In the following examples, the specificity of the hybridization reactions following solid phase PCR amplification was tested. Four cDNA target polynucleotides, human G3PDH, PKC-α, c-Raf, and Cyclin A, were selected for specific detection by amplification on a microarray.

a. Specific Amplification of G3PDH

An amine-coated glass chip was spotted with four different sense strand primers from human genes G3PDH, PKC-α, c-Raf, and Cyclin A. The human G3PDH gene was specifically amplified and detected following DNA polymerase chain reaction using 1 pg (about $4 \times 10^5$ copies) of single strand phagemid DNA from pG3PDH with 25 pMol G3PDH antisense primer in solution.

5 μg mRNA was isolated from OVC 1.1 cells and used for reverse-transcription of single-strand cDNA. The SuperScript II kit (Life Technology Inc.) was used to carry out the reverse transcription reaction. 0.5 μg prepared cDNA was used as template to run an asymmetric PCR with 25 pMol universal primer (Uni-1) in the reaction solution, and various concentrations of specific primers for four target genes, hu G3PDH, PKC-α, cyclin-A and c-Raf, were immobilized on different spots of a microarray. The PCR reaction was conducted according to conditions and procedures as described in Example 1(a) above.

Figure 7:
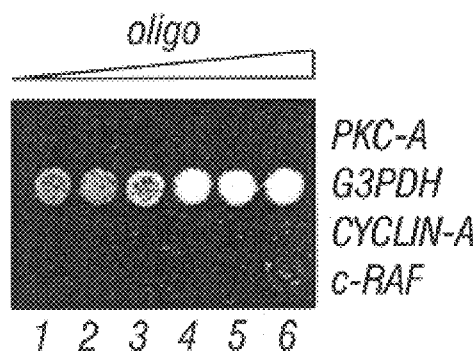
FIG. 7 illustrates the specificity of hybridization following solid phase amplification using G3PDH target cDNA as template.

The results are shown in FIG. 7. The spotting primer concentrations, from columns 1 to 6, are 3.125, 6.25, 12.5, 25, 50 and 100 pmol/μl respectively. The illuminated spots indicate that only the amplification products of hu G3PDH can be detected in spots containing hu G3PDH primers, suggesting strong specificity of the assay.

b. Specific Amplification of G3PDH and c-Raf

An amine-coated glass chip was spotted with four different sense strand primers from human genes G3PDH, PKC-α, c-Raf, and Cyclin A. The human G3PDH gene was specifically amplified and detected following DNA polymerase chain reaction using 100 ng of c-Raf DNA, and 1 pg (about $4 \times 10^5$ copies) of single strand phagemid DNA from pG3PDH with 25 pMol G3PDH antisense primer but no c-Raf antisense primer in solution.

Figure 8:
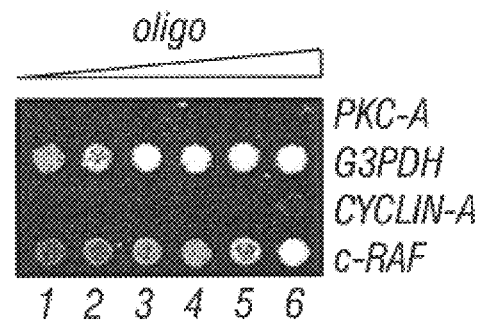
FIG. 8 illustrates the specificity of hybridization following solid phase amplification using G3PDH and c-Raf target cDNAs as template.

Various concentrations of specific primers for four target genes, hu G3PDH, PKC-α, cyclin-A and c-Raf, were immobilized on different spots of a microarray. The PCR reaction was conducted according to conditions and procedures as described in Example 1(a) above. The results are shown in FIG. 8. The spotting primer concentrations, from columns 1 to 6, are 3.125, 6.25, 12.5, 25, 50 and 100 pmol/μl respectively. The illuminated spots indicate that the amplification products of hu G3PDH can be detected in spots containing hu G3PDH primers with stronger signals than the c-Raf detected in spots containing c-Raf primers, suggesting strong specificity of the assay as well as the enhanced sensitivity of the asymmetric PCR on hu G3PDH.

c. Specific Amplification of G3PDH, PKC-α, c-Raf; and Cyclin A

An amine-coated glass chip was spotted with four different sense strand primers from human genes G3PDH, PKC-α, c-Raf, and Cyclin A. All four genes were specifically amplified and detected following DNA polymerase chain reaction using the four gene populations as templates and 25 pMol each of the four antisense strand primers in solution.

Figure 9:
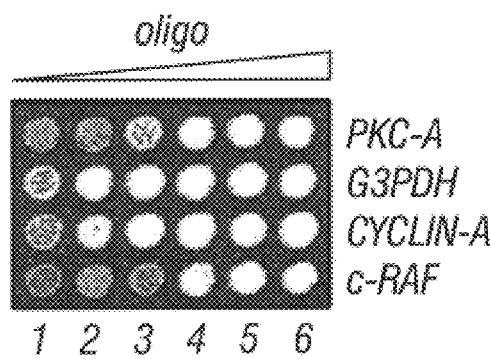
FIG. 9 illustrates the specificity of hybridization following solid phase amplification using four different target cDNA as templates.

The results are shown in FIG. 9. The spotting primer concentrations, from columns 1 to 6, are 3.125, 6.25, 12.5, 25, 50 and 100 pmol/μl respectively. The illuminated spots indicate that all four amplification products can be detected.

d. Test for Specific Amplification on Fetal Brain cDNA Library Gene Expression Analysis A human fetal brain cDNA library (Stratagene) was used as a template for DNA PCR on a microarray chip. 0.05 μg of prepared cDNA was used as template to run PCR amplification with 25 pMol universal primer (Uni-1) in the reaction solution on a microarray spotted with various concentrations of specific primers for four target genes, hu G3PDH, PKC-α, cyclin-A and c-Raf. The PCR reaction was conducted according to conditions and procedures as described in Example 1(a) above.

Figure 10:
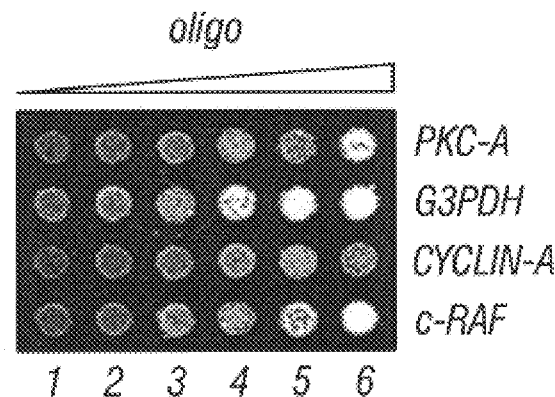
FIG. 10 illustrates the specificity of hybridization following solid phase amplification of target mRNA from a fetal brain library using four different target cDNA as templates.

The results are shown in FIG. 10. The spotting primer concentrations, from columns 1 to 6, are 3.125, 6.25, 12.5, 25, 50 and 100 pmol/μl respectively. The data matched the hybridization results on an HO1 ExpressChip™ (Mergen, Ltd., San Leandro, Calif.) using the same DNA samples indicating very little distortion of relative signals by solid phase amplification.

e. Test for Specific Amplification on OVC1.1 Cell Gene Expression Analysis

An amine-coated glass chip was spotted with four different sense strand primers from human genes G3PDH, PKC-α, c-Raf, and Cyclin A. The human G3PDH gene was specifically amplified and detected following DNA polymerase chain reaction using 1 pg (about $4 \times 10^5$ copies) of single strand phagemid DNA from pG3PDH with 25 pMol G3PDH antisense primer in solution.

5 μg mRNA were isolated from OVC 1.1 cells and reverse-transcribed to single-strand cDNA using the SuperScript II kit (Life Technology Inc.). 0.05 μg of cDNA was used as template to run a PCR reaction with 25 pMol universal primer (Uni-1) in the reaction solution, and various concentrations of sense-strand oligonucleotide primers for the target genes, hu G3PDH, PKC-α and cyclin-A, immobilized on different spots of a microarray.

Figure 11:
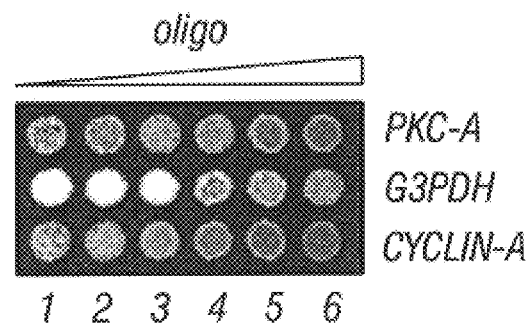
FIG. 11 illustrates the specificity of hybridization following solid phase amplification of target mRNA from a OVC1.1 cells using three different target cDNA as templates.

The results are shown in FIG. 11. The spotting primer concentrations, from columns 1 to 6, are 3.125, 6.25, 12.5, 25, 50 and 100 pmol/μl respectively. The illuminated spots indicate very little distortion of relative signals by solid phase amplification.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for detecting multiple target polynucleotides in a sample, the method comprising the steps of:
   a) providing an array of oligonucleotide primers wherein each array contains at least two groups of oligonucleotide primers immobilized on discrete areas of a solid phase support, each group of oligonucleotide primers selectable for a particular target polynucleotide and comprising primer sequences complementary to a sequence of the particular target polynucleotide;

b) contacting the array with a reaction mixture comprising a sample, said sample containing or suspected of containing multiple target polynucleotides, said reaction mixture further comprising reagents suitable for polynucleotide hybridization and amplification;

c) performing a first round of polymerase-mediated polynucleotide amplification, whereby the target polynucleotides serve as initial templates for the synthesis of optionally detectable nascent polynucleotides which are extended from the immobilized primers;

d) performing a second round of polymerase-mediated polynucleotide amplification in the presence of solution phase primers, wherein the solution phase primers serve as primers and the immobilized nascent polynucleotide strands from step c) serve as templates for the synthesis of detectable amplification products which are extended from the solution phase primers; and e) detecting the presence and quantity of the synthesized polynucleotides which are captured on discrete areas of the solid phase support via corresponding immobilized primers.

2. The method of claim 1, wherein the solution phase primers are specific for particular target polynucleotides.

3. The method of claim 1, wherein the solution phase primers are universal primers.

4. The method of claim 3, wherein the universal primers are oligo-dT primers.

5. The method of claim 3, wherein the universal primers comprise SP6 promoters, T3 promoters or T7 promoters.

6. The method of claim 1, wherein the reaction mixture comprises a detectable label that is incorporated into the nascent polynucleotides, thereby making the nascent polynucleotides detectable.

7. The method of claim 6, wherein the detectable label is a fluorescent molecule.

8. The method of claim 6, wherein the detectable label is a biotinylated-dNTP or a digoxigenin-dNTP.

9. The method of claim 1, wherein the reaction mixture comprises a first detectable label that specifically binds to a second label which is incorporated into the nascent polynucleotides, thereby making the nascent polynucleotides detectable.

10. The method of claim 9, wherein the second label is a biotinylated-dNTP and first detectable label is a streptavidin conjugated to a fluorescent molecule or an enzymatically activatable molecule.

11. The method of claim 9, wherein the second label is a digoxigenin-dNTP and first detectable label is an anti-digoxigenin antibody conjugated to a fluorescent molecule or an enzymatically activatable molecule.

12. The method of claim 1, wherein the array comprises from at least about 100 to about 100,000 groups of immobilized oligonucleotide primers.

13. The method of claim 12, wherein the array comprises at least about 1,000 groups of immobilized oligonucleotide primers.

14. The method of claim 13, wherein the array comprises at least about 10,000 groups of immobilized oligonucleotide primers.

15. The method of claim 1, wherein the solid phase support is made of material selected from the group consisting of glass, plastics, synthetic polymers, ceramic and nylons.

16. The method of claim 1, wherein the polymerase is Taq DNA polymerase, TthI DNA polymerase, Tne DNA polymerase, Tma DNA polymerase, Pfu DNA polymerase, Vent DNA polymerase or any other thermostable DNA polymerase.

17. A method for detecting and comparing the expression patterns of multiple target polynucleotides from at least two different biological sources, the method comprising the steps of:

a) providing an array of multiple groups of oligonucleotide primers immobilized on a solid phase support, each group of oligonucleotide primers being selected for a particular target polynucleotide and comprising primers complementary to a sequence of a target polynucleotide, wherein target polynucleotides from each biological source contain a covalently linked sequence tag unique to the biological source;

b) contacting the array with a sample comprising multiple target polynucleotides from at least two different biological sources;

c) performing a first round of polymerase-mediated polynucleotide amplification under conditions suitable for polynucleotide hybridization and amplification, whereby the target polynucleotides from the different biological sources serve as initial templates for synthesis of complementary nascent polynucleotide strands which are extended from the immobilized primers;

d) performing a second round of polymerase-mediated polynucleotide amplification in the presence of solution phase sequence tags that are unique to each biological source, wherein the solution phase sequence tags serve as primers and the immobilized nascent polynucleotide strands from step c) serve as templates for the synthesis of new amplification products which are extended from the solution phase sequence tags; and e) detecting and comparing the immobilized amplification products of the target polynucleotides from the different biological sources.

18. The method of claim 17, wherein the different biological sources are different cells.

19. The method of claim 17, wherein the different biological sources are different tissues.

20. The method of claim 17, wherein the different biological sources are different individuals.

21. The method of claim 17, wherein the different biological sources are different species.

22. The method of claim 17, wherein the amplification products of the target polynucleotides from different biological sources are detected by different labels.

23. The method of claim 22, wherein the labels are fluorescent molecules.

24. The method of claim 22, wherein the labels are biotin or digoxigenin.

25. The method of claim 17, wherein the sequence tags are universal primers.

26. The method of claim 25, wherein the universal primers comprise SP6 promoters, T3 promoters or T7 promoters.

27. A kit for detecting multiple target polynucleotides in a sample, comprising:

a) a solid phase support comprising a plurality of immobilized and separate populations of oligonucleotide primers each population selected to hybridize to a different target polynucleotide, wherein each primer is suitable for conducting a polymerase chain reaction with a specific target polynucleotide to amplify the polynucleotide;

b) one or more populations of solution phase primers each population selected to hybridize to amplification products of one or more target polynucleotides, wherein the solution phase primers are suitable to serve as primers for the synthesis of detectable amplification products which are extended from the solution phase primers;

c) reagents necessary for conducting a polymerase mediated amplification reaction on the solid support; and d) detection means for detecting amplified polynucleotides on the support.

28. The kit of claim 27, wherein the detection means comprises a label that is incorporated into the amplified polynucleotide during the amplification reaction.

29. The kit of claim 27, wherein the detection means comprises a first label that specifically binds to a second label which is incorporated into the amplified polynucleotide during the amplification reaction.

30. A system for detecting and comparing the expression patterns of multiple target polynucleotides from at least two different biological sources, comprising:

an array comprising at least two groups of oligonucleotide primers immobilized on discrete areas of a solid phase support, each group of oligonucleotide primers being selected for a particular target polynucleotide and comprising primers complementary to a sequence of the particular target polynucleotide, wherein each group is identifiable by its position on the solid support; and a supply of target polynucleotides from at least two biological sources wherein target nucleotides from each biological source contain a tag that is unique to the biological source.

31. The system of claim 30, wherein the array comprises from at least about 100 to about 100,000 groups of immobilized oligonucleotide primers.

32. The system of claim 31, wherein the array comprises at least about 1,000 groups of immobilized oligonucleotide primers.

33. The system of claim 32, wherein the array comprises at least about 10,000 groups of immobilized oligonucleotide primers.

34. The system of claim 30, wherein the tag is a covalently linked sequence tag.

* * * * *